United States Patent [19]

Denker

[11] Patent Number: 5,674,271

[45] Date of Patent: Oct. 7, 1997

[54] CATHETER WITH STEERABLE STYLET

[76] Inventor: Stephen Denker, 5240 N. Lake Dr.., Whitefish Bay, Wis. 53217

[21] Appl. No.: 749,293

[22] Filed: Nov. 14, 1996

[51] Int. Cl.$^6$ ............................................. A61N 1/05
[52] U.S. Cl. ................................. 607/119; 607/122
[58] Field of Search ................................ 607/119, 122, 607/127; 128/642; 600/129, 146, 147, 131, 139, 136; 606/41, 46, 47

[56] References Cited

U.S. PATENT DOCUMENTS

| | | | |
|---|---|---|---|
| 4,026,303 | 5/1977 | Babotai | 128/418 |
| 4,136,703 | 1/1979 | Wittkampf | 128/419 |
| 4,357,947 | 11/1982 | Littleford | 128/786 |
| 4,401,127 | 8/1983 | Littleford | 128/786 |
| 4,498,482 | 2/1985 | Williams | 158/786 |
| 4,905,666 | 3/1990 | Fukuda | 600/146 |
| 5,168,864 | 12/1992 | Shockey | 600/131 |
| 5,242,441 | 9/1993 | Avitall | 607/122 |
| 5,318,525 | 6/1994 | West et al. | 607/122 |
| 5,360,441 | 11/1994 | Otten | 607/122 |
| 5,397,321 | 3/1995 | Houser et al. | 607/122 |
| 5,423,879 | 6/1995 | Nyman | 607/122 |
| 5,480,421 | 1/1996 | Otten | 607/122 |

Primary Examiner—Lee S. Cohen
Assistant Examiner—David M. Ruddy
Attorney, Agent, or Firm—Quarles & Brady

[57] ABSTRACT

An electrode lead for intracorporeal stimulation of body tissue includes a tubular electrode cable and a removable stylet therein for guiding the cable during insertion through a blood vessel and heart chambers. The electrode cable has a flexible conductor extending through an insulating sheath which has a tubular shape forming a lumen. An exposed electrode, to which the conductor connects, closes a distal end of the electrode cable, while the proximate end of the electrode cable is grasped by an operator. The stylet extends from the distal cable end to the proximate end and engages the operator. The stylet has an outer tube forming a stylet lumen with a longitudinal axis and an inner wire which extends through the stylet lumen. The inner wire and outer tube are attached on one side of the longitudinal axis adjacent their distal ends, so that movement of the inner wire with respect to the outer tube causes curvature of the outer tube which in turn bends the electrode cable for steering through the blood vessel. After the electrode cable has been positioned at the desired location for stimulation, the stylet is removed.

10 Claims, 1 Drawing Sheet

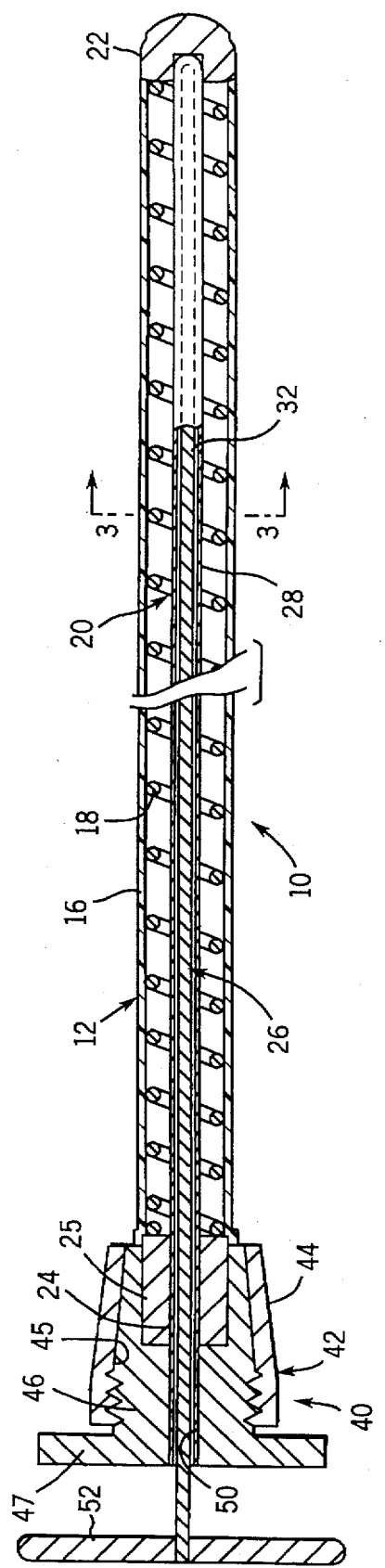
FIG. 1
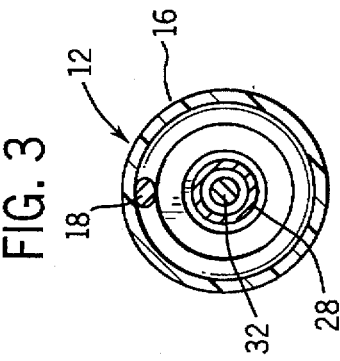
FIG. 3
FIG. 2

CATHETER WITH STEERABLE STYLET

BACKGROUND OF THE INVENTION

The present invention relates to medical and surgical devices, and more particularly to steerable electrode leads for intracorporeal stimulation of body tissue.

Electrode devices are generally known in the art for intracardial stimulation of the heart and include a hollow electrode cable containing an elongated, flexible conductor within an insulating outer layer. In use, the cable extends through a blood vessel into the patient's heart where the tip of the cable, having an electrode terminal, contacts the heart wall. Once in place a pacing circuit applies an electrical pulse to the cable in order to stimulate the heart muscle at the location of the electrode terminal.

It is of great importance for the electrode cable to be sufficiently pliant so that during implantation it is able to advance into the patient's heart via a blood vessel and follow the course of the blood vessel without damaging the vessel wall. In most instances, the electrode cable is introduced through the blood vessel and heart chambers using a stylet, which is inserted into the lumen of the electrode cable. The stylet is made of a metal or plastic material possessing the desired stiffness necessary to advance the electrode cable through the blood vessel. At difficult passages where the cable must bend sharply, the stylet often is retracted slightly from the cable, so that the distal end of the electrode cable displays maximum pliancy. After such a passage has been negotiated, the stylet is again advanced to the distal end of the electrode cable in order to push this end through the next portion of the blood vessel. As used herein, "distal end" refers to the end of the electrode cable having the terminal at which stimulation occurs and refers to the end of the stylet which when inserted fully into the electrode cable is at the cable's distal end.

At other times after partially inserting the electrode cable, the stylet is withdrawn completely from the cable which remains in place, and the stylet is manually bent into a desired curvature required to negotiate the next portion of the passage. The newly bent stylet is reinserted completely into the distal end of the electrode cable, and the assembly then is pushed forward into the next passage portion. This withdrawal, bending and reinsertion of the stylet may be repeated several times in order to properly guide the electrode cable into the atrium or ventricle of the heart. Care must be exercised by the physician so that the electrode cable and the blood vessel are not damaged by the repeated removal and reinsertion of the stylet.

Once the electrode cable is properly in place with the distal terminus imbedded or in contact with the proper portion of the heart wall, the stylet is withdrawn.

SUMMARY OF THE INVENTION

A general object of the present invention is to provide a stylet which is steerable without requiring withdrawal from the electrode cable each time a change in shape or direction is desired.

Another object of the present invention is to provide a stylet which will guide the electrode cable through the blood vessels and heart chambers without damaging those anatomical features or the electrode cable.

The above objects are achieved by a steerable electrode lead for intracorporeal stimulation of body tissue which has a tubular electrode cable with a lumen through which a stylet removably extends. The electrode cable has a flexible conductor extending through an insulating sheath that has a first end with an exposed terminal for contacting the body tissue, and has an open second end.

The stylet projects from the open second end of the electrode cable, and has an outer tube forming a stylet lumen with a longitudinal axis. The stylet includes an inner wire which extends through the stylet lumen and is fastened to the outer tube, so that movement of the inner wire along the longitudinal axis with respect to the outer tube causes curvature of the outer tube and the electrode cable. Preferably the inner wire is attached to the outer tube on only one side of the longitudinal axis proximate to the distal end.

The preferred embodiment of the steerable electrode lead includes an operator with grip engaging the outer tube of the stylet and the second end of the electrode cable. The operator also includes a handle which is attached to the inner wire and movable with respect to the grip. The user of the steerable electrode lead is able to produce bending of the distal end of the stylet and electrode cable by moving the handle with respect to the grip.

In that manner the electrode cable can be steered through a patient's blood vessel and heart chambers without having to repeatedly remove, reconfigure and reinsert the stylet. Thus the chances of damaging the electrode cable during insertion are reduced.

BRIEF DESCRIPTION OF THE INVENTION

FIG. 1 is a longitudinal cross-sectional view through a steerable electrode lead according to the present invention;

FIG. 2 is an enlarged longitudinal cross-sectional view of the distal end of the electrode lead in FIG. 1; and FIG. 3 is a radial cross-sectional view taken along lines 3—3 of FIG. 1.

DETAILED DESCRIPTION OF THE INVENTION

With initial reference to FIGS. 1 and 3 a steerable electrode lead 10, such as is used in cardiac pacemakers, includes an electrode cable 12 and a stylet 26. The electrode cable 12 has an outer sheath 16 in the form of a tube of electrically insulating material and a flexible electrical conductor 18 helically wound within the outer sheath 16 along the longitudinal axis of the electrode lead. The electrode cable forms a lumen 20 extending along its length between a closed distal end 22 and an open proximate end 24. A tubular metal pin 25 is attached to the conductor 18 at the proximate end 24 of the cable 12 for connecting the cable to a pacing device or other type of medical apparatus after implantation in a patient.

During insertion of the electrode cable into a patient, the stylet 26 is inserted into the open proximate end 24 and extends through the lumen 20 of the electrode cable 12 to the distal end 22. The stylet 26 has an outer tube 28 with a closed distal end 30, shown in FIG. 2, which is rounded to guide insertion through the cable. Alternatively, the distal end 30 could be open. The stylet also includes an inner wire 32 within the stylet lumen of the outer tube 28.

Referring to FIG. 2, the distal end 22 of the electrode cable 12 terminates at an electrode terminal 34 of conductive material connected to the conductor 18. The electrode terminal 34 closes the distal end 22 of the electrode cable by engaging the outer sheath 16. The electrode terminal 34 has a curved surface which aids in guiding the electrode lead 10 through the blood vessels of the patient during insertion. Other types of electrode terminals 34 commonly used with cardiac pacing leads may be utilized as well.

The inner wire 32 extends to the closed distal end 30 of the outer tube 28. The two stylet components are fastened together at point 36 on one side only of the longitudinal axis of the electrode cable. Adhesive or other fastening techniques may be utilized to attach the inner wire 32 to the outer tube 28.

Referring again to FIG. 1, the proximate end 24 of the electrode cable 12 is connected to an operator 40 during insertion of the electrode cable into the patient. The operator 40 comprises a grip 42 formed by a chuck 44 having a partially threaded, partially tapered aperture 45 into which a collet 46 is threaded. The collet 46 has a knob 47 and an aperture 50 into which the metal pin 25 at the proximate end of the cable is received. When the chuck 44 is screwed tightly onto the collet 46, the collet grasps the metal pin 25 securing the operator grip 42 onto the proximate end 24 of electrode cable 12.

The stylet 26 extends through an aperture 50 in the collet 46 with the outer tube 28 being bonded to the aperture wall and thus attached to the operator grip 42. The stylet's inner wire 32 extends through the operator grip 42 and projects from the collet 46. This proximate end of the inner wire 32 has a handle 52 attached thereto.

The electrode lead 10 is assembled as shown in the drawings prior to insertion of the cable 12 into the patient. The distal end 22 of the assembly is inserted through an incision in a blood vessel of the patient and pushed into the blood vessel toward the heart. As a sharply bending passage of the blood vessel is encountered, the physician grasps the grip 42 of operator 40 in one hand and with the other hand manipulates the handle 52. By pulling and pushing the handle 52 toward and away from the grip 42, the inner wire 32 is moved longitudinally with respect to the stylet's outer tube 28. Because the outer tube 28 and inner wire 32 are fastened together at point 36 on only one side of the longitudinal axis near the distal end of stylet 26, longitudinal movement of the inner wire 32 causes the outer tube 28 to bend upward when the handle 52 is pushed inward and to bend downward when the handle is pulled away from the grip 42, in the illustrated orientation of the components. The amount of longitudinal movement between the stylet's outer tube 28 and inner wire 32 determines the degree of bending. As the distal end of the stylet 26 bends, its outer surface engages the conductor 18 of electrode cable 12 thus causing a similar bending of the electrode cable. A physician may manipulate the operator 40 by feel or by viewing the distal end 22 on a fluoroscope.

Thus the novel stylet 26 enables the distal end 22 of the electrode cable 12 to be steered through passages of the patient's blood vessels and heart without having to repeatedly remove the stylet, reconfigure a bend at the stylet tip and reinsert the stylet into the electrode cable. Not only is the present stylet easier and faster to use, the potential for damage to the electrode cable by repeated insertion and removal has been eliminated.

When the electrode terminal 34 at the distal end of the electrode cable has been properly positioned where stimulation is desired, the grip chuck 44 is unscrewed from the collet 46 thereby releasing the metal pin 25. With the pin 25 released, the stylet 26 can be extracted from the electrode cable 12. Next the collet 44 is pulled off of the proximate end 24 of the cable 12 which then is attached to a pacing device or other type of medical apparatus.

I claim:

1. A steerable electrode lead for intracorporeal stimulation of body tissue, the electrode lead comprising:

an electrode cable with a flexible conductor and having a tubular shape forming a lumen, the electrode cable possessing a first end with an exposed terminal for contacting the body tissue and having an open second end; and a stylet removably inserted into the lumen through the open second end of the electrode cable, and having an outer tube forming a stylet lumen with a longitudinal axis, the stylet including an inner wire which extends through the stylet lumen and is fastened to the outer tube so that movement of the inner wire along the longitudinal axis with respect to the outer tube causes curvature of the outer tube and the electrode cable.

2. The steerable electrode lead as recited in claim 1 wherein the outer tube has one end projecting from the second end of the electrode cable, and the inner wire has a proximate end projecting from the one end of the outer tube; and further comprising an operator with a grip engaging the one end of the outer tube and a handle engaging the proximate end of the inner wire.

3. The steerable electrode lead as recited in claim 2 wherein the grip includes a mechanism to grasp the electrode cable.

4. The steerable electrode lead as recited in claim 3 wherein the a mechanism comprises a collet within a chuck.

5. The steerable electrode lead as recited in claim 1 wherein said inner wire is fastened to the outer tube on only one side of the longitudinal axis.

6. The steerable electrode lead as recited in claim 1 wherein the electrode cable comprises a tubular sheath with the flexible conductor located within the tubular sheath.

7. The steerable electrode lead as recited in claim 6 wherein the flexible conductor extends in a helix along the tubular sheath.

8. A steerable electrode lead for intracorporeal stimulation of body tissue, the electrode lead comprising:

an electrode cable having a flexible conductor extending through an insulating sheath which has a tubular shape forming a lumen, the insulating sheath having a first end with an exposed terminal for contacting the body tissue and having an open second end;

a stylet removably inserted into the lumen through the open second end of the electrode cable, and having an outer tube forming a stylet lumen having a longitudinal axis and a distal end, the stylet including an inner wire which extends through the stylet lumen and is fastened to the outer tube on only one side of the longitudinal axis proximate to the distal end, wherein movement of the inner wire along the longitudinal axis with respect to the outer tube causes curvature of the outer tube; and an operator having grip a engaging the outer tube of the stylet and the second end of the electrode cable, and having a handle attached to the inner wire and movable with respect to the grip.

9. The steerable electrode lead as recited in claim 8 wherein the electrode cable comprises an outer sheath with the flexible conductor located within the outer sheath.

10. The steerable electrode lead as recited in claim 9 wherein the flexible conductor extends in a helix within the outer sheath.

* * * * *